United States Patent [19]

Clark et al.

[11] Patent Number: 5,334,391
[45] Date of Patent: Aug. 2, 1994

[54] INTRACELLULARLY CLEAVABLE COMPOUNDS

[75] Inventors: Brian R. Clark, Redwood City; Bishwajit Nag, Pacifica, both of Calif.

[73] Assignee: Anergen, Inc., Redwood City, Calif.

[21] Appl. No.: 890,187

[22] Filed: May 29, 1992

Related U.S. Application Data

[62] Division of Ser. No. 523,334, May 14, 1990, Pat. No. 5,169,934.

[51] Int. Cl.$^5$ .............................................. A61K 9/127
[52] U.S. Cl. .................................. 424/450; 428/402.2
[58] Field of Search .................. 424/450; 436/839; 428/402.2; 516/2, 12, 14, 21; 530/327, 387

[56] References Cited

U.S. PATENT DOCUMENTS

| | | | |
|---|---|---|---|
| 4,460,560 | 7/1984 | Tokes | 424/1.1 |
| 4,839,175 | 6/1989 | Guo | 424/450 |
| 4,847,240 | 7/1989 | Ryser | 514/12 |
| 4,861,581 | 8/1989 | Epstein | 424/1.1 |
| 4,873,088 | 10/1989 | Mayhew | 424/450 |

Primary Examiner—G. S. Kishore
Attorney, Agent, or Firm—Townsend and Townsend Khourie and Crew

[57] ABSTRACT

Intracellularly cleavable derivatives of toxic compounds including antibiotics are described.

3 Claims, 1 Drawing Sheet

INTRACELLULARLY CLEAVABLE COMPOUNDS

This is a division of application Ser. No. 07/523,334 filed May 14, 1990, now a U.S. Pat. No. 5,169,934.

FIELD OF THE INVENTION

This invention relates to novel, intracellularly cleavable, disulfide linked derivatives of ligands, including particularly the anthracycline glycoside antibiotics exemplified by doxorubicin (Adriamycin), doxorubicinol, daunorubicin and daunorubicinol; to therapeutically active compositions such as liposomes which include such derivatives and to mammalian, including human, diagnostic and therapeutic procedures in which such derivatives and compositions are utilized.

BACKGROUND OF THE INVENTION

Many drugs such as doxorubicin, a potent cancer therapeutic agent, and Amphotericin B, the most effective drug presently known for a broad range of fungal infections, are highly toxic.

Liposome systems have been proposed as bloodstream delivery systems to provide controlled release and to minimize toxic side effects of a variety of encapsulated drugs, such as doxorubicin and Amphotericin B.

Various limitations on intravenous liposome drug delivery have been recognized. Importantly included among these limitations are unduly rapid release or leakage of the encapsulated drug from the liposome and insipid uptake of blood circulatory liposomes by the reticuloendothelial system (RES) which comprises circulating and fixed macrophages.

SUMMARY OF THE INVENTION

This invention provides novel, all internalizable intracellularly cleavable derivatives of diagnostically and therapeutically useful ligands. Such derivatives are efficient bloodstream delivery systems for the cleavable ligand. These derivatives may be parenterally administered as such or as associated with liposomes or biodegradable microspheres.

In its broader aspects, the invention includes derivatives of releasable ligands which may bind to any of a variety of targets. The ligand moieties are joined to the balance of the novel derivatives of the invention by an intracellularly cleavable disulfide linkage. The novel cell internalizable derivatives of the invention may have the formula

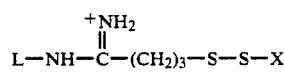

in which L is or is included in an intracellularly releasable ligand moiety and X is any organic radical. Preferably, X provides a function to be internalized by or attached to cells. X may enable detection, modify cellular function or serve some other diagnostic or therapeutic purpose. The novel derivatives of the invention are prepared by known chemical methods as will be apparent to those skilled in the art.

One important embodiment of the invention comprises novel disulfide linked ligand-peptide derivatives. Another embodiment of the invention designed for liposomal delivery of therapeutic or diagnostic agents includes disulfide linked ligand-lipid derivatives which may be incorporated into liposome bilayers by standard techniques. Such derivatives may be anchored to the liposome bilayer by the lipid moiety.

DETAILED DESCRIPTION OF THE INVENTION

A. The Ligands

The nature of the ligands useful as moieties of the novel derivatives of the invention is determined by the function that the ligand is to perform after intracellular cleavage. In general, such ligands include, but are not limited to, receptor agonists, receptor antagonists, antineoplastic agents such as doxorubicin, peptides, poly and monoclonal antibodies, polynucleic acids, antitoxins, antifungal agents and enzyme inhibitors. The various cancer chemotherapeutic and antifungal ligands are described in the relevant patents and publications. Any peptide may be utilized that is a ligand for a natural receptor. Ligands useful to provide mucosal tissue retention are known to the art. See U.S. Pat. No. 4,839,175.

Figure 1:
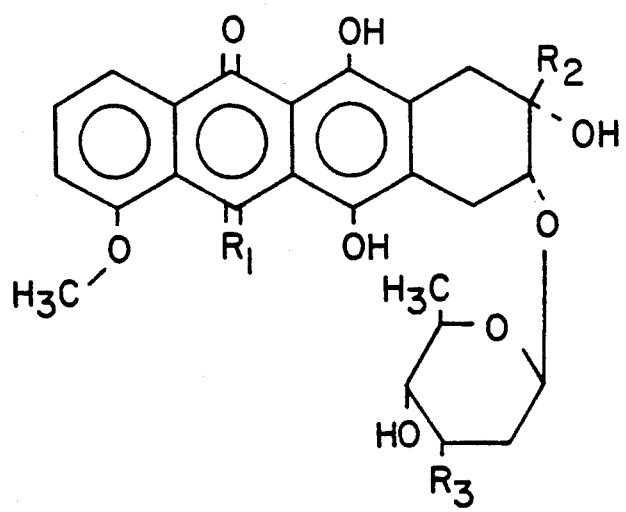
Figure 2:
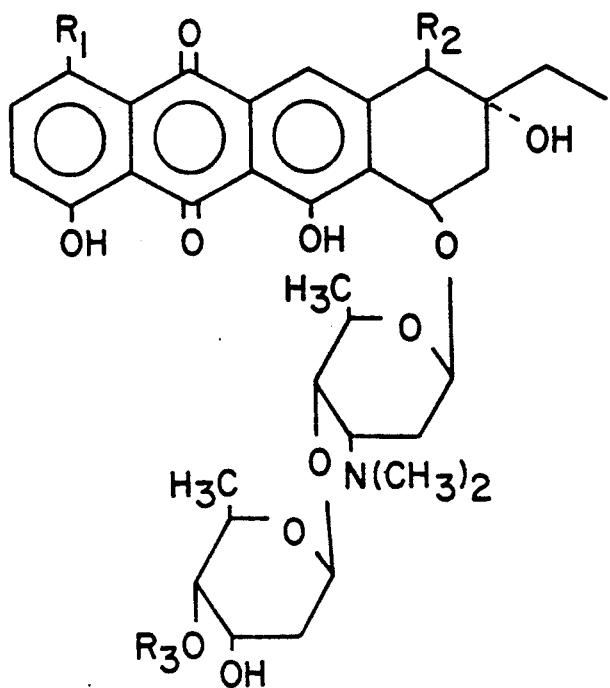

Anthracycline glycoside ligands useful in the invention include anthraquinone structures having one quinone and hydroquinone group on adjacent rings of the anthracene ring structure. Two groups of antineoplastic anthraquinones having these features are illustrated in FIGS. 1 and 2. Many other compounds of this type are described in the prior art.

Included in the FIG. 1 group are a number of clinically important antineoplastic drugs, such as doxorubicin, daunomycin, carcinomycin, N-acetyladriamycin, N-acetyldaunomycin, rubidasone, and 5-imidodaunomycin. Table I below gives the structure variations of these several class I drugs, in terms of the $R_1$, $R_2$ and $R_3$ groups in FIG. 1.

TABLE I

|  | $R_1$ | $R_2$ | $R_3$ |
|---|---|---|---|
| Adriamycin | =O | —CO—CH$_2$OH | —NH$_2$ |
| Daunomycin | =O | —CO—CH$_3$ | —NH$_2$ |
| N-Acetyladriamycin | =O | —CO—CH$_2$OH | —NH—CO—CH$_3$ |
| N-Acetyldaunomycin | =O | —CO—CH$_3$ | —NH—CO—CH$_3$ |
| Rubidazone | =O | —C—N—NH—C—CH$_3$O | —NH$_2$ |
| 5-Iminodaunomycin | =NH | —CO—CH$_3$ | —NH$_2$ |

Drugs in this class are known to have antineoplastic effects against a variety of cancers, including acute leukemia, breast cancer, Hodgkin disease, non-Hodgkin lymphomas and sarcomas.

A second group of anthracene glycosides, which are distinguished from the class I compounds by more complex (multimeric) amino glycoside residues, as seen in FIG. 2. These compounds share the same general therapeutic and toxicity properties of their class I counterparts. Representative Class II anthracene aminoglycosides are listed in Table II, with reference to the $R_1$, $R_2$ and $R_3$ groups shown in FIG. 2.

TABLE II

| Anthracycline | $R_1$ | $R_2$ | $R_3$ |
|---|---|---|---|
| Musettamycin | OH | COOCH$_3$ | H |
| Rudolfomycin | OH | COOCH$_3$ | Rednosamine |
| Aclaciaomycin | H | COOCH$_3$ | Cinerulose |
| Marcellomycin | OH | COOCH$_3$ | 2-Deoxyfucose |
| Descarbomethoxy-marcellomycin | OH | H | 2-Deoxyfucose |
| Descarbomethoxy-rudolfomycin | OH | H | Rednosamine |

B. The Intracellularly Cleavable Compounds

Intracellularly releasable peptides are known. See, e.g., Truet, et al. (1982) *EORTC Symposium*: "Promising New Anti-Cancer Agents in Clinical Trials" (Mathe, G., Ed.). Masson, Paris; Shen, et al. (1981) *Biochem. Biophys. Res. Comm.* 102:1048-1054; Blattler, et al. (1985) *Biochem.* 24:1517-1524; and Marsh, et al. (1987) *J.Biol.Chem.* in press.

Intracellular cleavage is imparted to the derivatives of this invention by a disulfide linkage which joins the ligand to the balance of the molecule. The chemistry for the production of such disulfide linkages is known. Appropriate chemistry can be selected for use with any desired ligand functionality. An appropriate functionality, e.g., a primary amine (—NH$_2$) substituent, an hydroxyl or a carboxyl may be provided in known chemical manner to ligands which lack such functionality.

For the purposes of this invention, ligands which have or which have been provided with amine, preferably primary amine, functionality are preferred.

The ligand amine functionality may be reacted with 2,2'-dithiodipyridine and 2'-iminothiolane in solution in dimethylacetamide to produce an N-(4-pyridyldithiobutyrimido) derivative of the ligand pursuant to Equation I in which L represents any ligand.

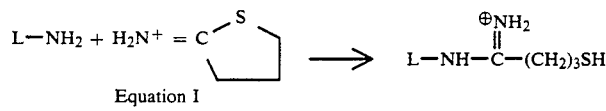

Equation I

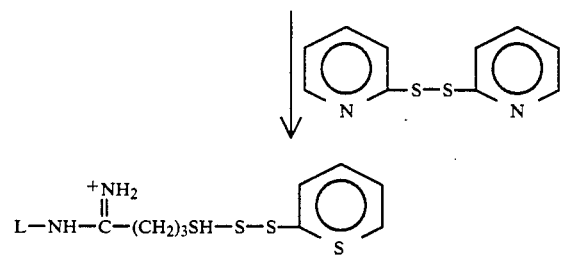

Compound A

Preferably L-NH$_2$ is an antineoplastic anthraquinone such as doxorubicin of the kind shown by FIG. 1 and FIG. 2. L-NH$_2$ may also be amphotericin B or another antifungal agent having an —NH$_2$ functionality.

The Compound A is utilized to produce a disulfide linked peptide or lipid derivative of the ligand. For example, the peptide derivative may be produced pursuant to Equation II by reacting Compound A with a mercaptopeptide X-SH in which X is any peptide.

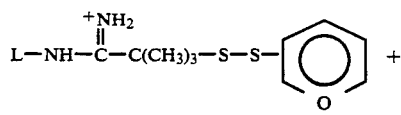

Compouond A
Equation II $$X-SH \xrightarrow{\text{Dimethylacetamide Solvent}}$$

$$X-S-S-(CH_2)_3-\overset{\overset{+NH_2}{\|}}{C}-NH-L$$
Compound B

X is preferably a peptide having from about 5 to 50 residues. X may also be an alkyl group R. R groups having from about 12 to 18 carbon atoms are miscible in liposome bilayers and serve as anchors for minimizing linkage when the derivatives of this invention are administered in the form of liposome delivery systems. Toxic peptides are preferred for some therapeutic uses.

When L or X is toxic, compounds having the formula of Compound B are toxic to cells when internalized. The toxicity is apparently consequent from cleavage of the disulfide link with consequent internal release of one or both the toxic moieties L and X.

EXAMPLE I

Synthesis of a Disulfide-Linked Doxorubicin (Adriamycin)-Lipid Derivative

The reactions are similar to those described for the disulfide-linked peptide-Adriamycin derivative. The Adriamycin intermediate described in Example I is used:

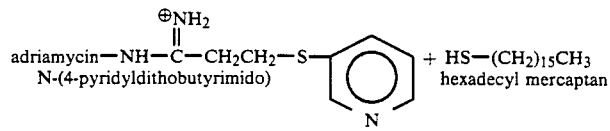

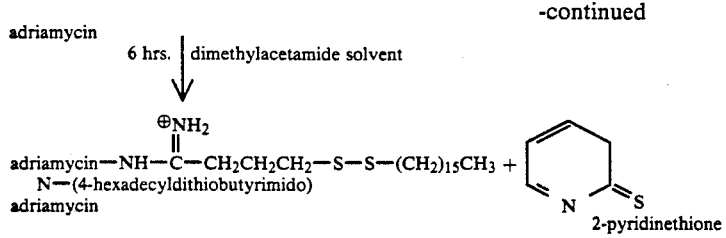

2-pyridinethione

The purified Adriamycin-lipid derivative is incorporated into liposomes by standard techniques. See, generally, Pozansky, M. J., et al. (1984) *Pharmacol. Rev.* 36:277–336. After uptake of the liposomes by cells, the internalized derivative is reductively cleaved by reduced glutathione, and the released, toxic Adriamycin is cytocidal.

C. The Liposomal Compositions of the Invention

Methods for preparing derivatives containing liposomes of this invention generally follow conventional liposome preparation methods. In one preferred method, vesicle forming lipids are taken up in a suitable organic solvent or solvent system and dried in vacuum or in an inert gas to a lipid film. The derivative is included in the lipids forming the film. The concentration of the derivative in the lipid solution is preferably in molar excess of the final maximum concentration of the drug in the liposome. The dried lipid/drug film is hydrated with a physiologically compatible medium, preferably physiological saline. The lipids hydrate to form a suspension of multilamellar vesicles (MLVs) whose size typically range from about 0.5 microns to at least about 10 microns. In general, the size distribution of MLVs in the above procedures can be shifted toward smaller sizes by hydrating the lipid film more rapidly, with shaking.

The liposome suspension may be sized to achieve a selective size distribution of vesicles in a size range less than about 1 micron and preferably between about 0.05 to 0.5 microns, and most preferably between about 0.005 and 0.2 microns. The sizing serves to eliminate larger liposomes and to produce a defined size range having optimal pharmacokinetic properties.

Several known techniques are available for reducing the sizes and size heterogeneity of liposomes. Sonicating a liposome suspension either by bath or probe sonication produces a progressive size reduction down to small unilamellar vesicles (SUVs) less than about 0.05 microns in size. A known sonicating procedure is preferably used in reducing liposome sizes to about 0.2 microns or less. Homogenization is another method which relies on shearing energy to fragment large liposomes into smaller ones. In a typical homogenization procedures, MVLs are recirculated through a standard emulsion homogeneizer until selected liposome sizes, typically between about 0.1 and 0.5 microns, are observed. In both methods, the particle size distribution can be monitored by conventional laser-beam particle size discrimination.

Extrusion of liposomes through a small-pore polycarbonate membrane is an effective method for reducing liposome sizes down to a relatively well-defined size distribution whose average in the range between about 0.1 and 1 micron, depending on the pore size of the membrane. Typically, the suspension is cycled through the membrane several times until the desired liposome size distribution is achieved. The liposomes may be extruded through successively smaller pore membranes, to achieve a gradual reduction in liposome size.

Centrifugation and molecular size chromatography are other methods which are available for producing a liposome suspension with particle sizes below a selected threshold less than 1 micron: These two methods both involve preferential removal of larger liposomes, rather than conversion of large particles to smaller ones. Liposome yields are correspondingly reduced.

D. The Therapeutic and Diagnostic Compositions

The invention importantly includes therapeutically and diagnostically useful compositions including the novel intracellularly releasable derivatives described herein. These derivatives may be administered to a mammalian subject, including humans. The prescribing physician will ultimately determine the appropriate dose for a given human subject. The dose can be expected to vary according to the age, weight, and response of the individual as well as the nature and severity of the patient's symptoms.

The mode of administration may determine the sites and cells in the organism to which the compound will be delivered. For instance, delivery to a specific site of infection may be most easily accomplished by topical application (if the infection is external, e.g., on areas such as eyes, skin, in ears, or on afflictions such as wounds or burns) or by absorption through epithelial or mucocutaneous linings (e.g., nasal, oral, vaginal, rectal, gastrointestinal, mucosa, etc. ). Such topical application may be in the form of creams or ointments. The liposome-entrapped materials can be administered alone but will generally be administered in admixture with a pharmaceutical carrier selected with regard to the intended route of administration and standard pharmaceutical practice. Such materials may be injected parenterally, for example, intravenously, intramuscularly, or subcutaneously. For parenteral administration, such materials are best used in the form of a sterile aqueous solution which may contain other solutes, for example, enough salts or glucose to make the solution isotonic.

For the oral mode of administration, compositions of this invention can be used in the form of tablets, capsules, lozenges, troches, powders, syrups, elixirs, aqueous solutions and suspensions, and the like. In the case of tablets, carriers w which can be used include lactose, sodium citrate, and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, certain sweetening and/or flavoring agents can be added.

The derivatives of this invention may also be used in diagnostic assays; in this case the amount of the composition used will depend on the sensitivity of the liposome-coupled derivative to the target components in the sample.

Unilamellar and multilamellar liposomes formed in conventional manner are useful in the invention. Vesicle forming lipids which generally include neutral and negatively charged phospholipids and a sterol such as cholesterol are appropriate. Vesicles comprising dipalmitoylphosphatidylcholine (DPPC) or distearoylphosphatidylcholine (DSPC) are preferred and may be prepared in known manner. See, e.g., Tomita, T., et al. (1989), *Biochim. Biophys. Acta* 978:185–190.

We claim:

1. A liposome having a compound anchored in the liposome bilayer said compound having the formula:

$$L-NH-\overset{\overset{+NH_2}{\|}}{C}-(CH_2)_3-S-S-(CH_2)_xCH_3$$

in which L is a doxorubicin moiety and X has a value of from 11 to 17.

2. A liposome as defined by claim 1 in which X in the formula of said compound has a value of 15.

3. A system for delivery of a cytocidal agent to a cell which system comprises a liposome composition including a compound having the formula of claim 1.

* * * * *